United States Patent
Sansone (10) Patent No.: US 8,367,656 B2
(45) Date of Patent: Feb. 5, 2013

(54) POLYMORPHS OF 7-[(3-CHLORO-6,11-DIHYDRO-6-METHYLDIBENZO[C,F][1,2]THIAZEPIN-11-YL)AMINO]HEPTANOIC ACID S,S DIOXIDE AND METHODS OF MAKING AND USING THE SAME

(75) Inventor: Matthew Sansone, Lowell, MA (US)

(73) Assignee: Janssen Biotech, Inc., Horsham, PA (US)

( * ) Notice: Subject to any disclaimer, the term of this patent is extended or adjusted under 35 U.S.C. 154(b) by 898 days.

(21) Appl. No.: 12/041,747

(22) Filed: Mar. 4, 2008

(65) Prior Publication Data

US 2008/0221081 A1    Sep. 11, 2008

Related U.S. Application Data

(60) Provisional application No. 60/892,947, filed on Mar. 5, 2007.

(51) Int. Cl.
*A61P 11/06* (2006.01)
*A61P 25/24* (2006.01)
*A61K 31/554* (2006.01)
*C07D 281/02* (2006.01)

(52) U.S. Cl. .................... 514/211.11; 540/549
(58) Field of Classification Search ............. 514/211.11; 549/549; 540/549
See application file for complete search history.

(56) References Cited

U.S. PATENT DOCUMENTS 3,758,528 A  9/1973 Malen et al.
4,766,114 A * 8/1988 Malen et al. ............. 514/211.13

FOREIGN PATENT DOCUMENTS

CA  995213  8/1976

OTHER PUBLICATIONS

Giannotti, D. et al.: New Dibenzothiadiazepine Derivatives with Antidepressant Activites. J. of Med. Chem. (1991) 34: 1356-1362.
Platzer, N. et al.: 1H and 13C NMR Studies of the Antidepressant Drug Tianeptine. Magnetic Resonance in Chem. (1992) 30: 1212-1219.
International Search Report dated Jun. 30, 2008, for International Application No. PCT/US08/55746.

* cited by examiner

*Primary Examiner* — Brenda Coleman
(74) *Attorney, Agent, or Firm* — Kiera K. Mathey (57) ABSTRACT

Disclosed herein are novel polymorphs of 7-[(3-chloro-6,11-dihydro-6-methyldibenzo[c,f][1,2]thiazepin-11-yl)amino] heptanoic acid S,S-dioxide. Also described herein are novel pharmaceutical compositions comprising one or more 7-[(3-chloro-6,11-dihydro-6-methyldibenzo[c,f][1,2]thiazepin-11-yl)amino]heptanoic acid S,S-dioxide polymorphs, methods of making, and related methods of treatment.

20 Claims, 8 Drawing Sheets

POLYMORPHS OF 7-[(3-CHLORO-6,11-DIHYDRO-6-METHYLDIBENZO[C,F][1,2]THIAZEPIN-11-YL)AMINO]HEPTANOIC ACID S,S DIOXIDE AND METHODS OF MAKING AND USING THE SAME

This Application claims benefit of priority under 35 U.S.C. 119(e) to U.S. Provisional Patent Application No. 60/892,914, filed Mar. 5, 2007.

FIELD OF THE INVENTION

The present invention relates to novel polymorphs of 7-[(3-chloro-6,11-dihydro-6-methyldibenzo[c,f][1,2]thiazepin-11-yl)amino]heptanoic acid S,S-dioxide. The invention also provides methods of using one or more 7-[(3-chloro-6,11-dihydro-6-methyldibenzo[c,f][1,2]thiazepin-11-yl)amino]heptanoic acid S,S-dioxide polymorphs in an oral dosage pharmaceutical composition and related methods of treatment.

BACKGROUND OF THE INVENTION

7-[(3-chloro-6,11-dihydro-6-methyldibenzo[c,f][1,2]thiazepin-11-yl)amino]heptanoic acid S,S-dioxide is a tricyclic compound also known as tianeptine. 7-[(3-chloro-6,11-dihydro-6-methyldibenzo[c,f][1,2]thiazepin-11-yl)amino]heptanoic acid S,S-dioxide is an antidepressant. The free form of 7-[(3-chloro-6,11-dihydro-6-methyldibenzo[c,f][1,2]thiazepin-11-yl)amino]heptanoic acid S,S-dioxide is amphoteric and an amorphous sodium salt is known in the art.

Synthesis of the 7-[(3-chloro-6,11-dihydro-6-methyldibenzo[c,f][1,2]thiazepin-11-yl)amino]heptanoic acid S,S-dioxide sodium salt is disclosed in U.S. Pat. No. 3,758,528. The 7-[(3-chloro-6,11-dihydro-6-methyldibenzo[c,f][1,2]thiazepin-11-yl)amino]heptanoic acid S,S-dioxide sodium salt (i.e., STABLON®) is currently approved in European countries for the treatment of one or more depressive disorders. STABLON® (7-[(3-chloro-6,11-dihydro-6-methyldibenzo[c,f][1,2]thiazepin-11-yl)amino]heptanoic acid S,S-dioxide sodium) has a short half-life and effective treatment often requires dosing multiple times each day.

Presently, a pharmaceutical composition of 7-[(3-chloro-6,11-dihydro-6-methyldibenzo[c,f][1,2]thiazepin-11-yl)amino]heptanoic acid S,S-dioxide sodium is generally dosed orally up to three times a day. This frequent oral dosing may lead to decreased compliance with the recommended dosing regimen. A controlled release pharmaceutical composition of 7-[(3-chloro-6,11-dihydro-6-methyldibenzo[c,f][1,2]thiazepin-11-yl)amino]heptanoic acid S,S-dioxide should enable better command over the release profile and consequently, a less demanding dosing regimen. A polymorph of 7-[(3-chloro-6,11-dihydro-6-methyldibenzo[c,f][1,2]thiazepin-11-yl)amino]heptanoic acid S,S-dioxide free form may be advantageous in the preparation of a controlled release pharmaceutical composition comprising 7-[(3-chloro-6,11-dihydro-6-methyldibenzo[c,f][1,2]thiazepin-11-yl)amino]heptanoic acid S,S-dioxide.

BRIEF SUMMARY OF THE INVENTION

The present invention relates to novel polymorphs of 7-[(3-chloro-6,11-dihydro-6-methyldibenzo[c,f][1,2]thiazepin-11-yl)amino]heptanoic acid S,S-dioxide. These novel polymorphs can exhibit improved properties relative to the currently marketed 7-[(3-chloro-6,11-dihydro-6-methyldibenzo[c,f][1,2]thiazepin-11-yl)amino]heptanoic acid S,S-dioxide sodium salt. Such improved properties can include, but are not limited to, crystallinity, purity, and physical stability. The invention also provides novel pharmaceutical compositions comprising one or more polymorphs of 7-[(3-chloro-6,11-dihydro-6-methyldibenzo[c,f][1,2]thiazepin-11-yl)amino]heptanoic acid S,S-dioxide, methods of making polymorphs of 7-[(3-chloro-6,11-dihydro-6-methyldibenzo[c,f][1,2]thiazepin-11-yl)amino]heptanoic acid S,S-dioxide, and related methods of treatment. For example, 7-[(3-chloro-6,11-dihydro-6-methyldibenzo[c,f][1,2]thiazepin-11-yl)amino]heptanoic acid S,S-dioxide Form 1 or 7-[(3-chloro-6,11-dihydro-6-methyldibenzo[c,f][1,2]thiazepin-1,1-yl)amino]heptanoic acid S,S-dioxide Form II provide an alternative in a pharmaceutical composition to the currently marketed form, 7-[(3-chloro-6,11-dihydro-6-methyldibenzo[c,f][1,2]thiazepin-11-yl)amino]heptanoic acid S,S-dioxide sodium salt.

7-[(3-chloro-6,11-dihydro-6-methyldibenzo[c,f][1,2]thiazepin-11-yl)amino]heptanoic acid S,S-dioxide has the following structure (I):

(I)

The polymorphs of 7-[(3-chloro-6,11-dihydro-6-methyldibenzo[c,f][1,2]thiazepin-11-yl)amino]heptanoic acid S,S-dioxide can be used to provide pharmaceutical compositions for the treatment of conditions known in the art, such as one or more depressive disorders, irritable bowel syndrome (IBS), attention deficit hyperactivity disorder (ADHD), and asthma.

For a better understanding of the present invention, together with other and further embodiments thereof, reference is made to the accompanying drawings and detailed description.

DETAILED DESCRIPTION OF THE INVENTION

The present invention relates to novel polymorphs of 7-[(3-chloro-6,11-dihydro-6-methyldibenzo[c,f][1,2]thiazepin-11-yl)amino]heptanoic acid S,S-dioxide. The properties of the polymorphs of 7-[(3-chloro-6,11-dihydro-6-methyldibenzo[c,f][1,2]thiazepin-11-yl)amino]heptanoic acid S,S-dioxide can be improved relative to one or more known forms of 7-[(3-chloro-6,11-dihydro-6-methyldibenzo[c,f][1,2]thiazepin-11-yl)amino]heptanoic acid S,S-dioxide, such as 7-[(3-chloro-6,11-dihydro-6-methyldibenzo[c,f][1,2]thiazepin-11-yl)amino]heptanoic acid S,S-dioxide sodium (the currently marketed form). Such improved properties can include, but are not limited to, crystallinity, purity, and physical stability. The invention also includes other forms of 7-[(3-chloro-6,11-dihydro-6-methyldibenzo[c,f][1,2]thiazepin-11-yl)amino]heptanoic acid S,S-dioxide including, but not limited to, co-crystals and amorphous forms. The invention also provides novel pharmaceutical compositions comprising these forms, methods of making these forms, and related methods of treatment.

The present invention comprises polymorphs of 7-[(3-chloro-6,11-dihydro-6-methyldibenzo[c,f][1,2]thiazepin-11-yl)amino]heptanoic acid S,S-dioxide. 7-[(3-chloro-6,11-dihydro-6-methyldibenzo[c,f][1,2]thiazepin-11-yl)amino]heptanoic acid S,S-dioxide has the following structure (I):

(I)

In a first embodiment, the present invention comprises a polymorph of 7-[(3-chloro-6,11-dihydro-6-methyldibenzo[c,f][1,2]thiazepin-11-yl)amino]heptanoic acid S,S-dioxide.

In a further embodiment, one or more polymorphs of 7-[(3-chloro-6,11-dihydro-6-methyldibenzo[c,f][1,2]thiazepin-11-yl)amino]heptanoic acid S,S-dioxide can be incorporated into a pharmaceutical composition. In a further embodiment, one or more polymorphs of 7-[(3-chloro-6,11-dihydro-6-methyldibenzo[c,f][1,2]thiazepin-11-yl)amino]heptanoic acid S,S-dioxide can be incorporated into a controlled release pharmaceutical composition.

In another embodiment, a polymorph of 7-[(3-chloro-6,11-dihydro-6-methyldibenzo[c,f][1,2]thiazepin-11-yl)amino]heptanoic acid S,S-dioxide can be incorporated into a pharmaceutical composition comprising two or more layers of said polymorph such that one layer is substantially released prior to the substantial release of another layer in vivo. In another embodiment, a polymorph of 7-[(3-chloro-6,11-dihydro-6-methyldibenzo[c,f][1,2]thiazepin-11-yl)amino]heptanoic acid S,S-dioxide can be incorporated into a pharmaceutical composition comprising pellets, wherein the pellets have varying extents or compositions of coating so as to enable release of the 7-[(3-chloro-6,11-dihydro-6-methyldibenzo[c,f][1,2]thiazepin-11-yl)amino]heptanoic acid S,S-dioxide over a substantially longer period of time than that of the currently available sodium salt (e.g., STABLON®).

In another embodiment, a polymorph of 7-[(3-chloro-6,11-dihydro-6-methyldibenzo[c,f][1,2]thiazepin-11-yl)amino]heptanoic acid S,S-dioxide can be incorporated into an osmotically active pharmaceutical composition suitable for oral administration. Osmotically active pharmaceutical compositions, osmotic pumps, osmotic drug delivery, and other osmotic technology suitable for oral administration can include, but are not limited to, OROSO® Push-Pull and OROSO® Tri-layer pharmaceutical compositions. In another embodiment, a polymorph of 7-[(3-chloro-6,11-dihydro-6-methyldibenzo[c,f][1,2]thiazepin-11-yl)amino]heptanoic acid S,S-dioxide can be incorporated into an OROSO® drug delivery system. Such controlled release pharmaceutical compositions comprising a polymorph of 7-[(3-chloro-6,11-dihydro-6-methyldibenzo[c,f][1,2]thiazepin-11-yl)amino]heptanoic acid S,S-dioxide, such as an osmotically active pharmaceutical composition suitable for oral administration, may lead to a longer lasting therapeutic effect than that of the 7-[(3-chloro-6,11-dihydro-6-methyldibenzo[c,f][1,2]thiazepin-11-yl)amino]heptanoic acid S,S-dioxide sodium salt in the currently marketed form.

Figure 1:
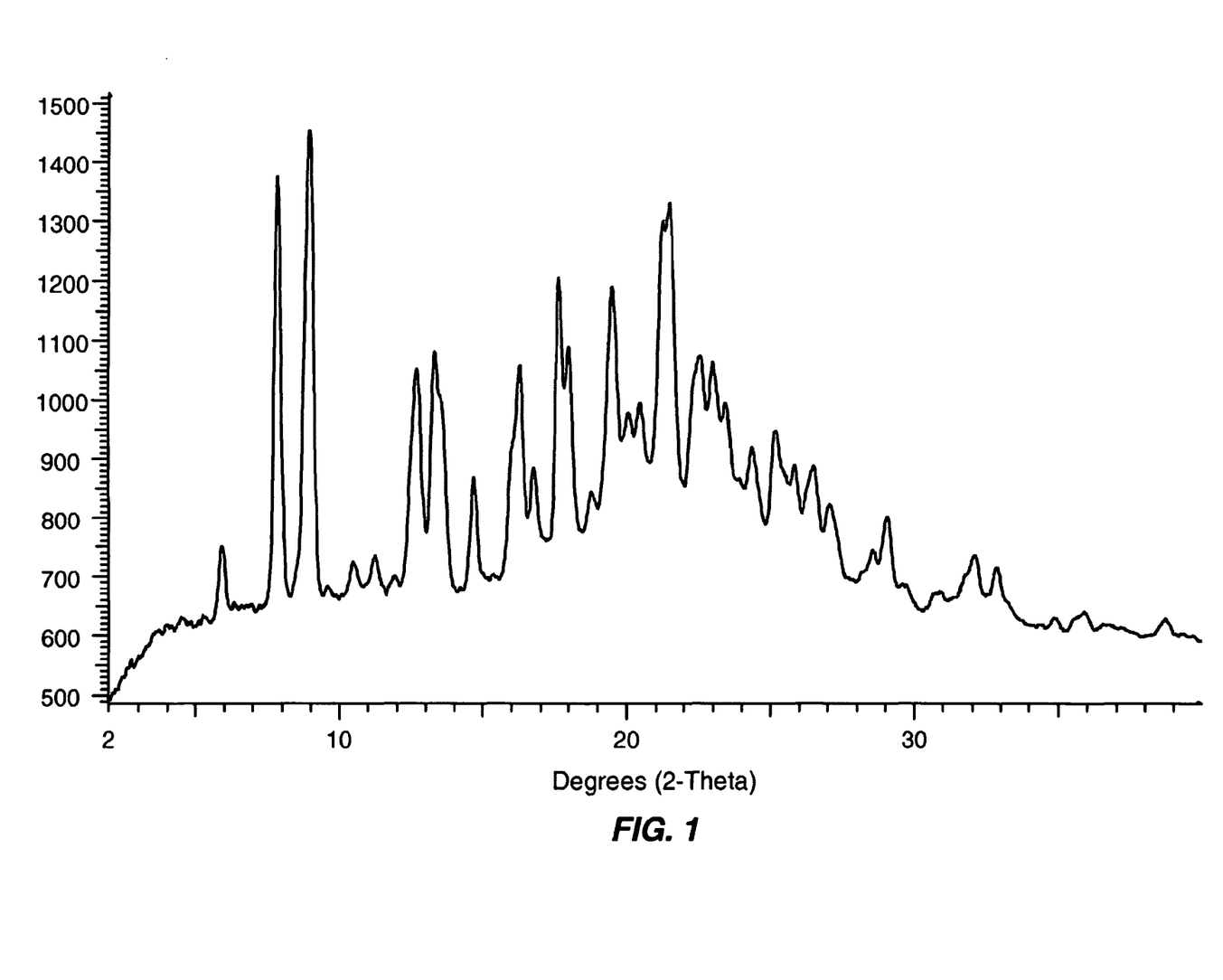
FIG. 1—PXRD diffractogram of 7-[(3-chloro-6,11-dihydro-6-methyldibenzo[c,f][1,2]thiazepin-11-yl)amino]heptanoic acid S,S-dioxide Form I FIG. 2—DSC thermogram of 7-[(3-chloro-6,11-dihydro-6-methyldibenzo[c,f][1,2]thiazepin-11-yl)amino]heptanoic acid S,S-dioxide Form I FIG. 3—TGA thermogram of 7-[(3-chloro-6,11-dihydro-6-methyldibenzo[c,f][1,2]thiazepin-11-yl)amino]heptanoic acid S,S-dioxide Form I FIG. 4—IR spectrum of 7-[(3-chloro-6,11-dihydro-6-methyldibenzo[c,f][1,2]thiazepin-11-yl)amino]heptanoic acid S,S-dioxide Form I FIG. 5—PXRD diffractogram of 7-[(3-chloro-6,11-dihydro-6-methyldibenzo[c,f][1,2]thiazepin-11-yl)amino]heptanoic acid S,S-dioxide Form II FIG. 6—DSC thermogram of 7-[(3-chloro-6,11-dihydro-6-methyldibenzo[c,f][1,2]thiazepin-11-yl)amino]heptanoic acid S,S-dioxide Form II
Figure 2:
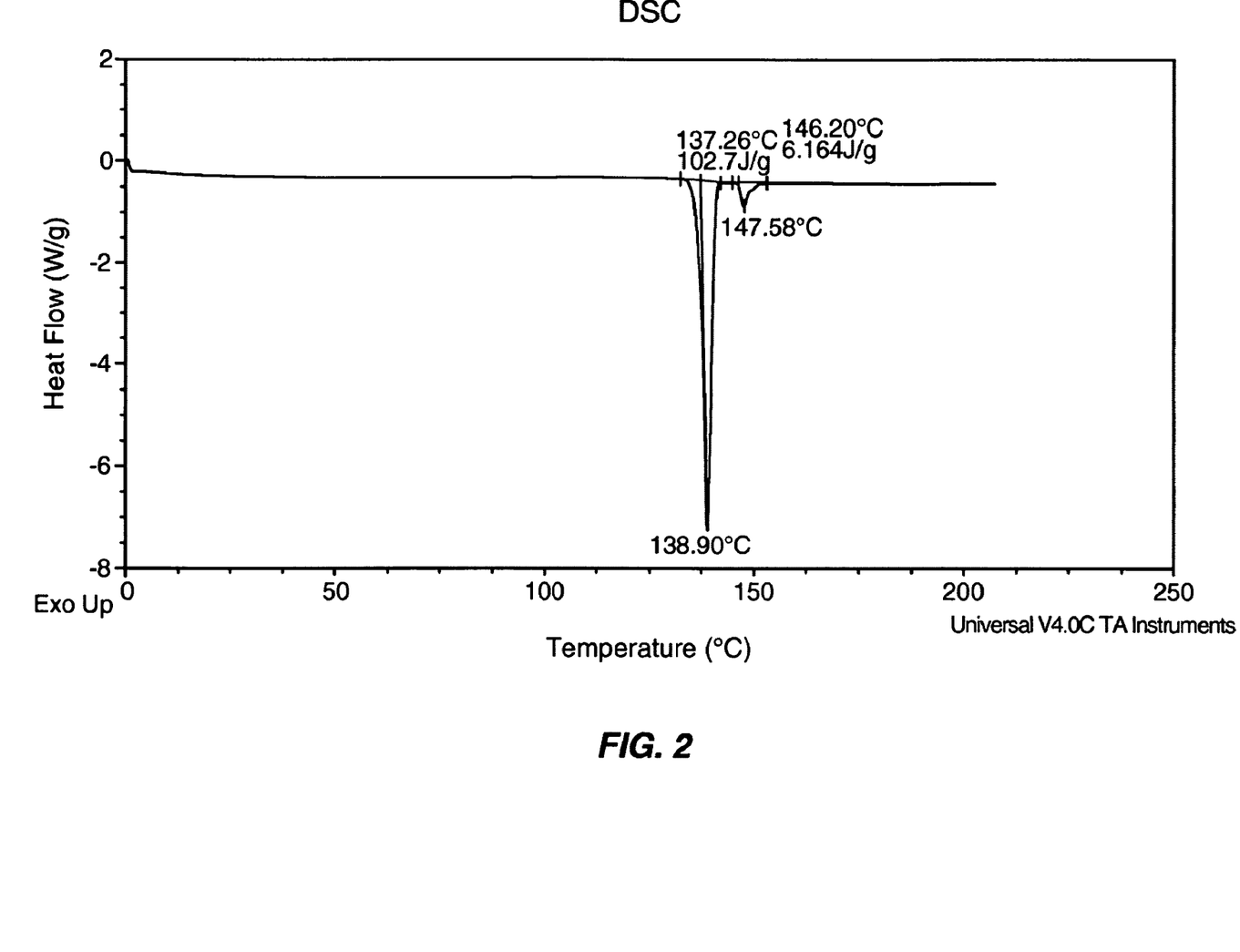
Figure 3:
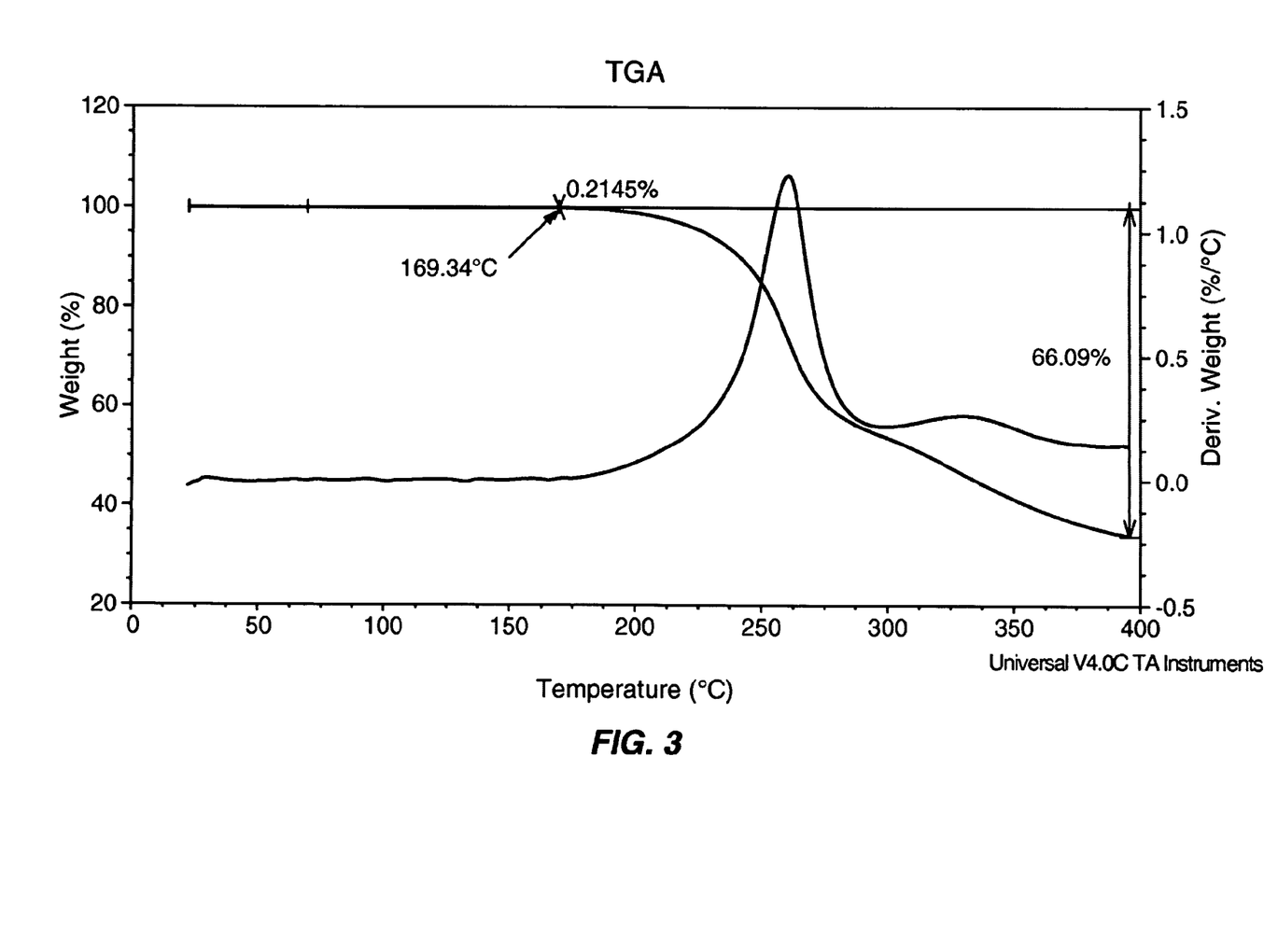
Figure 4:
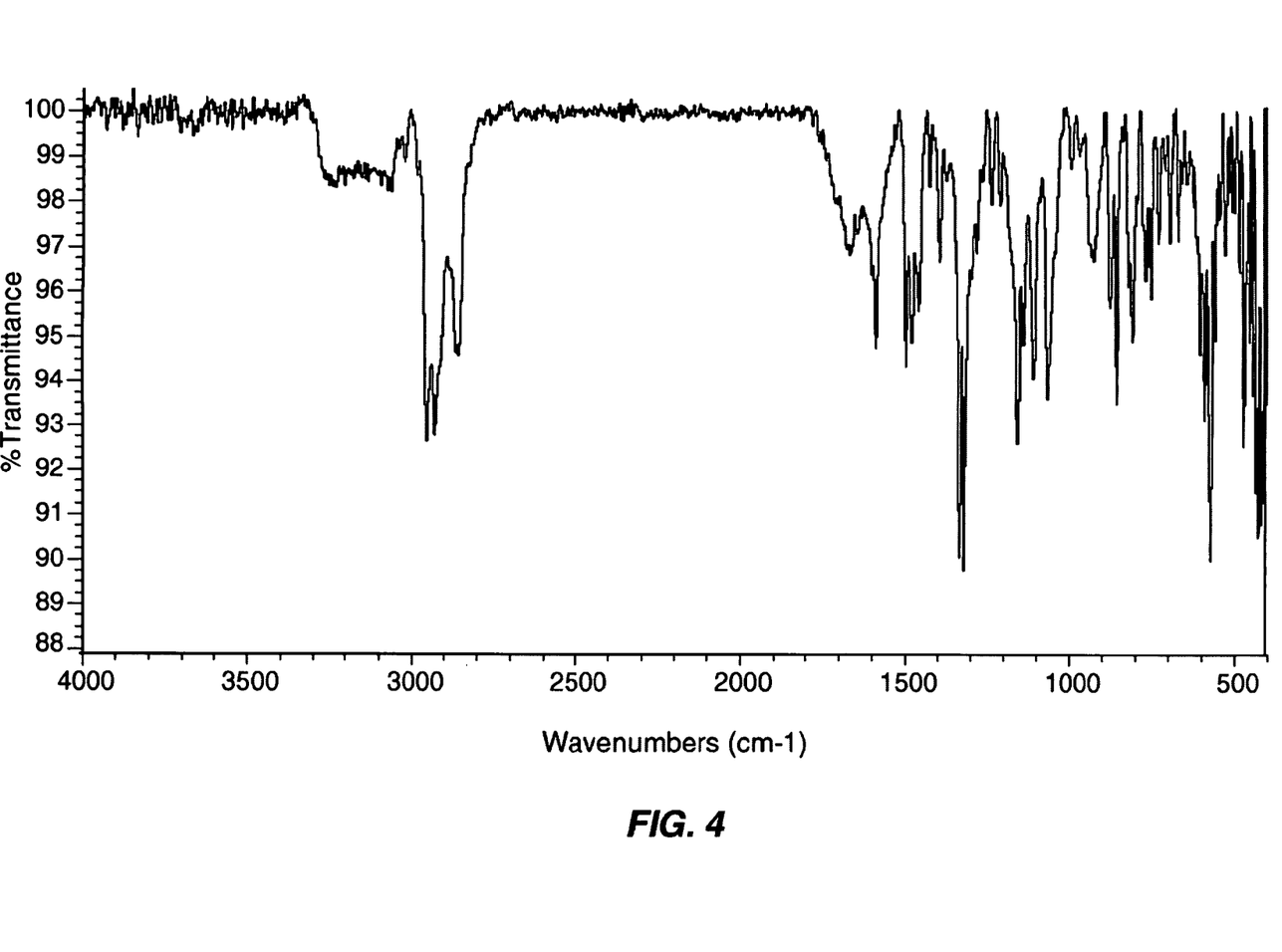

In another embodiment, the present invention comprises 7-[(3-chloro-6,1,1-dihydro-6-methyldibenzo[c,f][1,2]thiazepin-11-yl)amino]heptanoic acid S,S-dioxide Form I. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising a peak at about 5.89 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising a peak at about 7.82 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising a peak at about 8.93 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 7.82 and about 8.93 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89 and about 7.82 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 12.66 and about 13.32 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89, about 7.82, and about 8.93 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89, about 12.66, about 13.32, and about 17.64 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 7.82, about 8.93, about 12.66, about 13.32, and about 14.72 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89, about 7.82, about 8.93, and about 13.32 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 14.72, about 16.26, about 17.64, and about 19.50 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89, about 7.82, about 8.93, about 16.26, and about 19.50 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89, about 7.82, about 8.93, about 12.66, about 13.32, and about 14.72 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram comprising peaks at about 5.89, about 7.82, about 8.93, about 12.66, about 13.32, about 14.72, about 16.26, about 17.64, about 19.50, about 21.56, about 22.58, and about 25.19 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a PXRD diffractogram substantially similar to FIG. 1. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a DSC thermogram comprising an endothermic transition at about 139 degrees C. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a DSC thermogram substantially similar to FIG. 2. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits a TGA thermogram substantially similar to FIG. 3. In another embodiment, the present invention comprises 7-[(3-chloro-6,11-dihydro-6-methyldibenzo[c,f][1,2]thiazepin-11-yl)amino]heptanoic acid S,S-dioxide Form I, wherein said Form I exhibits an IR spectrum substantially similar to FIG. 4. In another embodiment, 7-[(3-chloro-6,11-dihydro-6-methyldibenzo[c,f][1,2]thiazepin-11-yl)amino]heptanoic acid S,S-dioxide Form I is incorporated into a controlled release pharmaceutical composition.

Figure 5:
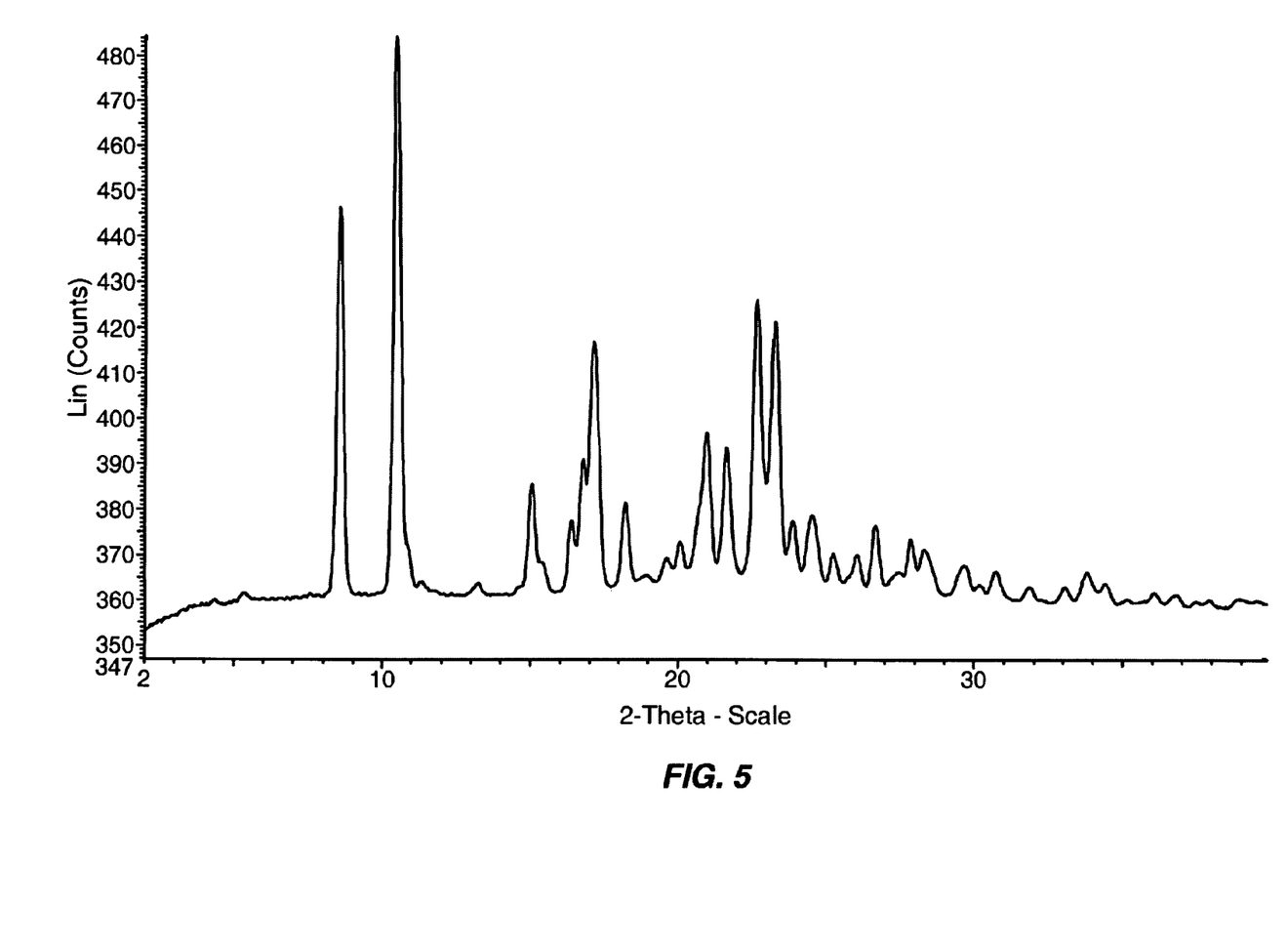
Figure 6:
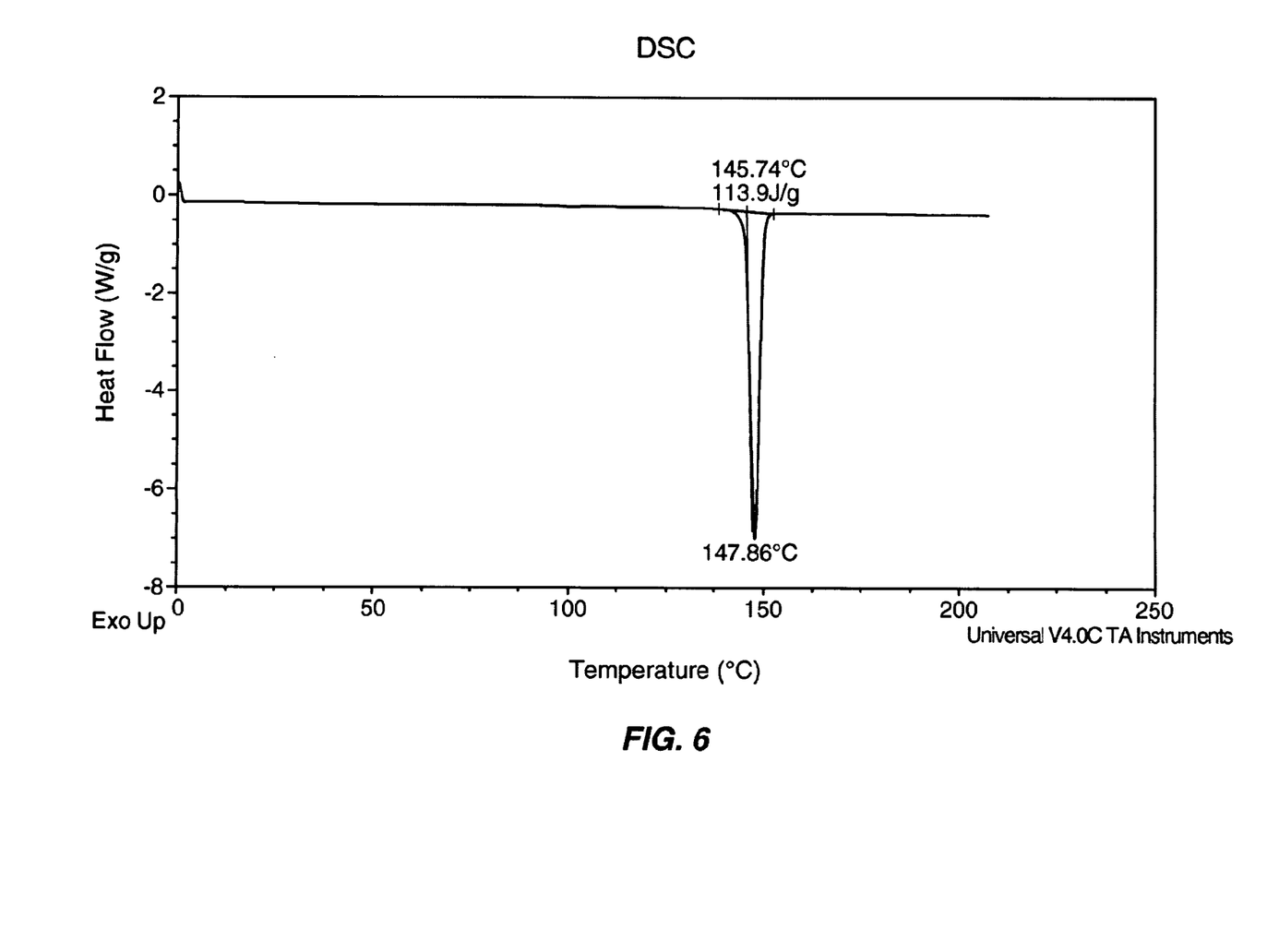
Figure 7:
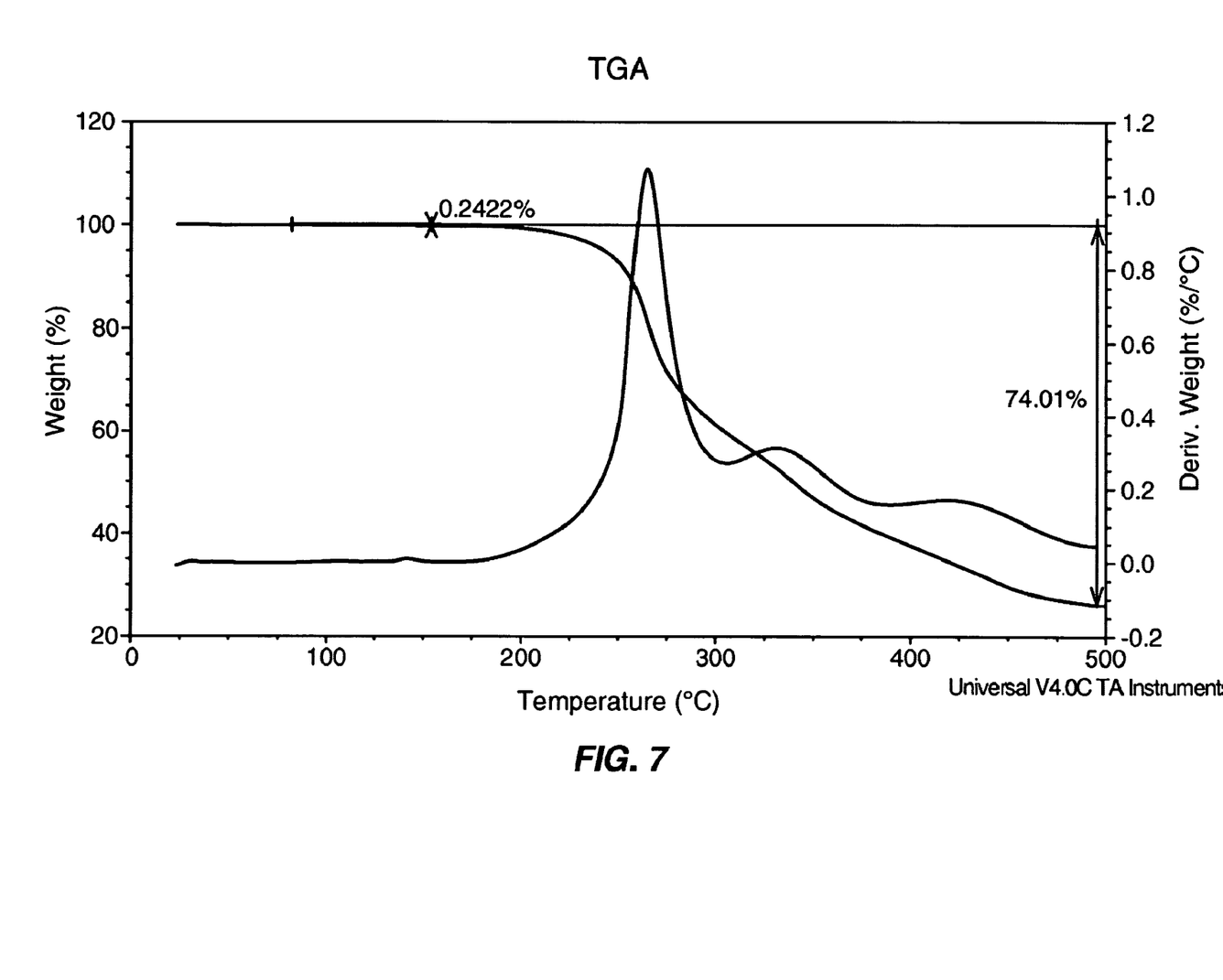
FIG. 7—TGA thermogram of 7-[(3-chloro-6,11-dihydro-6-methyldibenzo[c,f][1,2]thiazepin-11-yl)amino]heptanoic acid S,S-dioxide Form II FIG. 8—IR spectrum of 7-[(3-chloro-6,11-dihydro-6-methyldibenzo[c,f][1,2]thiazepin-11-yl)amino]heptanoic acid S,S-dioxide Form II
Figure 8:
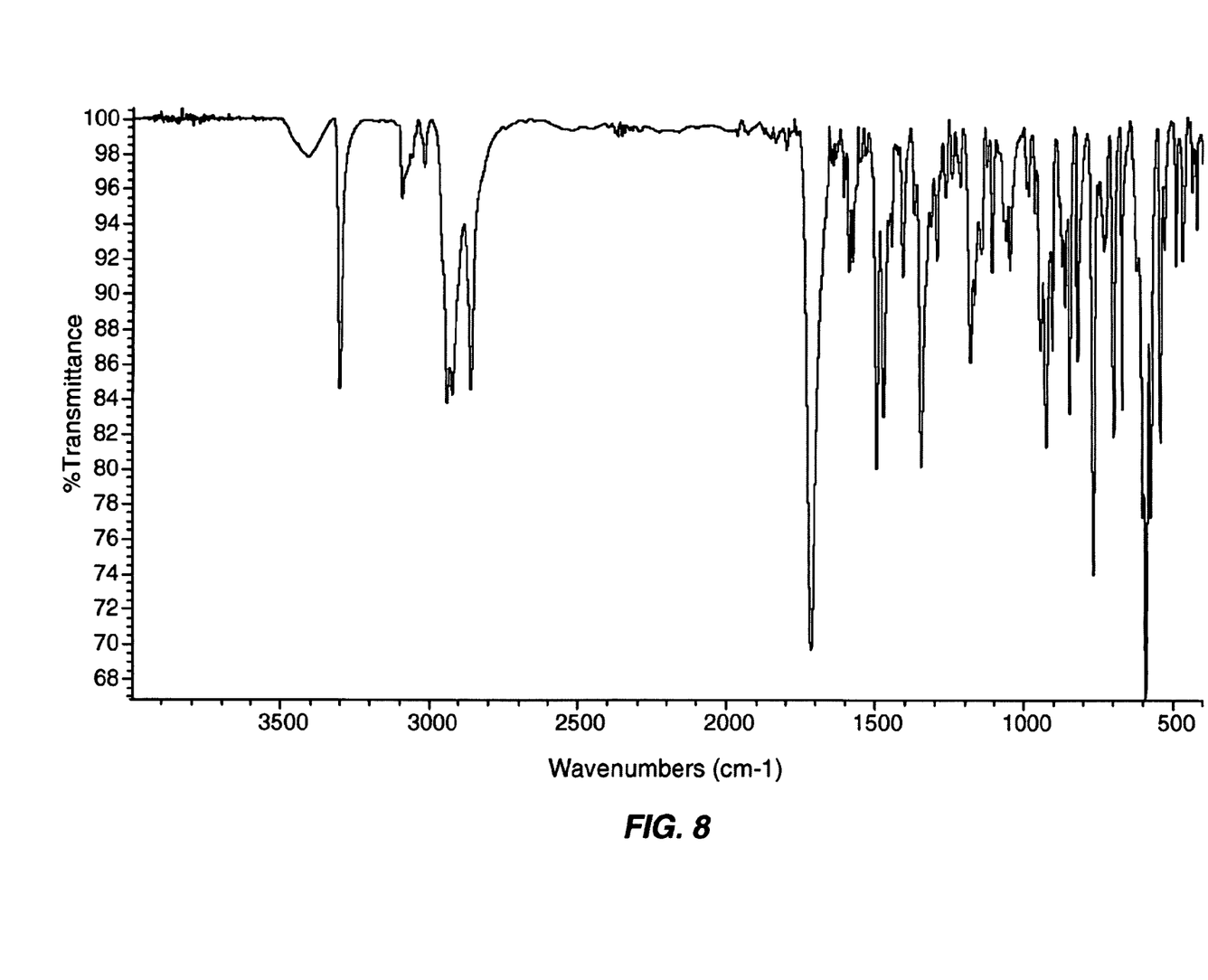

In another embodiment, the present invention comprises 7-[(3-chloro-6,1,1-dihydro-6-methyldibenzo[c,f][1,2]thiazepin-11-yl)amino]heptanoic acid S,S-dioxide Form II. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising a peak at about 8.52 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising a peak at about 10.46 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising a peak at about 15.05 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52 and about 10.46 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52 and about 17.14 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 10.46 and about 17.14 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52, about 10.46, and about 15.05 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 15.05, about 17.14, about 18.22, and about 20.99 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52, about 10.46, about 17.14, about 22.68, and about 23.35 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52, about 15.05, about 20.99, and about 21.66 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 10.46, about 17.14, about 18.22, and about 21.66 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52, about 10.46, about 15.05, about 17.14, and about 18.22 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52, about 10.46, about 15.05, about 17.14, about 18.22, and about 20.99 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram comprising peaks at about 8.52, about 10.46, about 15.05, about 17.14, about 18.22, about 20.99, about 21.66, about 22.68, about 23.35, about 23.88, about 24.55, and about 26.71 degrees 2-theta. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a PXRD diffractogram substantially similar to FIG. 5. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a DSC thermogram comprising an endothermic transition at about 148 degrees C. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a DSC thermogram substantially similar to FIG. 6. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits a TGA thermogram substantially similar to FIG. 7. In another embodiment, the present invention comprises 7-[(3-chloro-6,11-dihydro-6-methyldibenzo[c,f][1,2]thiazepin-11-yl)amino]heptanoic acid S,S-dioxide Form II, wherein said Form II exhibits an IR spectrum substantially similar to FIG. 8. In another embodiment, 7-[(3-chloro-6,11-dihydro-6-methyldibenzo[c,f][1,2]thiazepin-11-yl)amino]heptanoic acid S,S-dioxide Form II is incorporated into a controlled release pharmaceutical composition.

In another embodiment, the present invention comprises 7-[(3-chloro-6,1,1-dihydro-6-methyldibenzo[c,f][1,2]thiazepin-11-yl)amino]heptanoic acid S,S-dioxide Form I, and methods of making and using the same. In another embodiment, the present invention comprises 7-[(3-chloro-6,11-dihydro-6-methyldibenzo[c,f][1,2]thiazepin-11-yl)amino]heptanoic acid S,S-dioxide Form II, and methods of making and using the same.

In another embodiment, the present invention provides a method of making a polymorph of 7-[(3-chloro-6,1,1-dihydro-6-methyldibenzo[c,f][1,2]thiazepin-11-yl)amino]heptanoic acid S,S-dioxide, comprising:
(a) providing 7-[(3-chloro-6,11-dihydro-6-methyldibenzo[c,f][1,2]thiazepin-11-yl)amino]heptanoic acid S,S-dioxide sodium salt; and
(b) contacting said 7-[(3-chloro-6,11-dihydro-6-methyldibenzo[c,f][1,2]thiazepin-11-yl)amino]heptanoic acid S,S-dioxide sodium salt with an appropriate acid so as to desalify said sodium salt;
(c) contacting the desalified mixture from step (b) with an appropriate solvent; and
(d) crystallizing said polymorph of 7-[(3-chloro-6,1,1-dihydro-6-methyldibenzo[c,f][1,2]thiazepin-11-yl)amino]heptanoic acid S,S-dioxide.

In a specific embodiment, a solvent is added to said 7-[(3-chloro-6,11-dihydro-6-methyldibenzo[c,f][1,2]thiazepin-11-yl)amino]heptanoic acid S,S-dioxide sodium salt prior to said appropriate acid. In another embodiment, step (b) is completed in the presence of a solvent such that a solution is formed prior to crystallization of the 7-[(3-chloro-6,11-dihydro-6-methyldibenzo[c,f][1,2]thiazepin-11-yl)amino]heptanoic acid S,S-dioxide polymorph. In another embodiment, step (b) is completed in the presence of a solvent such that a suspension is formed prior to crystallization of the 7-[(3-chloro-6,11-dihydro-6-methyldibenzo[c,f][1,2]thiazepin-11-yl)amino]heptanoic acid S,S-dioxide polymorph. In a specific embodiment, said polymorph of 7-[(3-chloro-6,11-dihydro-6-methyldibenzo[c,f][1,2]thiazepin-11-yl)amino]heptanoic acid S,S-dioxide is 7-[(3-chloro-6,11-dihydro-6-methyldibenzo[c,f][1,2]thiazepin-11-yl)amino]heptanoic acid S,S-dioxide Form I. In certain embodiments, an appropriate solvent is selected from the group consisting of: acetone, ethanol, nitromethane, methanol, acetonitrile, dichloromethane, water, and tetrahydrofuran (THF). In another embodiment, an appropriate solvent comprises a mixture of any two or more solvents, including, but not limited to, acetone, ethanol, nitromethane, methanol, acetonitrile, dichloromethane, water, and tetrahydrofuran.

In another embodiment, the present invention provides a method of making a polymorph of 7-[(3-chloro-6,11-dihydro-6-methyldibenzo[c,f][1,2]thiazepin-11-yl)amino]heptanoic acid S,S-dioxide, comprising:
(a) providing 7-[(3-chloro-6,11-dihydro-6-methyldibenzo[c,f][1,2]thiazepin-11-yl)amino]heptanoic acid S,S-dioxide Form I;
(b) contacting said 7-[(3-chloro-6,11-dihydro-6-methyldibenzo[c,f][1,2]thiazepin-11-yl)amino]heptanoic acid S,S-dioxide Form I with an appropriate solvent; and
(c) crystallizing said polymorph of 7-[(3-chloro-6,11-dihydro-6-methyldibenzo[c,f][1,2]thiazepin-11-yl)amino]heptanoic acid S,S-dioxide.

In another embodiment, step (b) is completed in the presence of a solvent such that a solution is formed prior to crystallization of the 7-[(3-chloro-6,11-dihydro-6-methyldibenzo[c,f][1,2]thiazepin-11-yl)amino]heptanoic acid S,S-dioxide polymorph. In another embodiment, step (b) is completed in the presence of a solvent such that a suspension is formed prior to crystallization of the 7-[(3-chloro-6,11-dihydro-6-methyldibenzo[c,f][1,2]thiazepin-11-yl)amino]heptanoic acid S,S-dioxide polymorph. In a specific embodiment, said polymorph of 7-[(3-chloro-6,11-dihydro-6-methyldibenzo[c,f][1,2]thiazepin-11-yl)amino]heptanoic acid S,S-dioxide is 7-[(3-chloro-6,11-dihydro-6-methyldibenzo[c,f][1,2]thiazepin-11-yl)amino]heptanoic acid S,S-dioxide Form II. In certain embodiments, a solvent is selected from the group consisting of: acetone, ethanol, nitromethane, methanol, acetonitrile, dichloromethane, water, and tetrahydrofuran (THF). In another embodiment, a solvent comprises a mixture of any two or more solvents, including, but not limited to, acetone, ethanol, nitromethane, methanol, acetonitrile, dichloromethane, water, and tetrahydrofuran.

The 7-[(3-chloro-6,11-dihydro-6-methyldibenzo[c,f][1,2]thiazepin-11-yl)amino]heptanoic acid S,S-dioxide sodium salt can be prepared by one or more methods known in the art, including, but not limited to, the method in U.S. Pat. No. 3,758,528.

In one embodiment of the present invention, an amount of a polymorph of 7-[(3-chloro-6,11-dihydro-6-methyldibenzo[c,f][1,2]thiazepin-11-yl)amino]heptanoic acid S,S-dioxide effective to modulate a mammal's physiology and/or to treat a mammal is administered to said mammal. In one aspect, the polymorph of 7-[(3-chloro-6,11-dihydro-6-methyldibenzo[c,f][1,2]thiazepin-11-yl)amino]heptanoic acid S,S-dioxide is administered in an amount sufficient to effect modulation of a mammal's physiology and/or treatment.

In another embodiment, a method of treating a mammal suffering from depression is provided, comprising administering to said mammal an effective amount of a polymorph of 7-[(3-chloro-6,11-dihydro-6-methyldibenzo[c,f][1,2]thiazepin-11-yl)amino]heptanoic acid S,S-dioxide. In another embodiment, a method of treating a mammal suffering from irritable bowel syndrome is provided, comprising administering to said mammal an effective amount of a polymorph of 7-[(3-chloro-6,11-dihydro-6-methyldibenzo[c,f][1,2]thiazepin-11-yl)amino]heptanoic acid S,S-dioxide. In another embodiment, a method of treating a mammal suffering from attention deficit hyperactivity disorder is provided, comprising administering to said mammal an effective amount of a polymorph of 7-[(3-chloro-6,11-dihydro-6-methyldibenzo[c,f][1,2]thiazepin-11-yl)amino]heptanoic acid S,S-dioxide. In another embodiment, a method of treating a mammal suffering from asthma is provided, comprising administering to said mammal an effective amount of a polymorph of 7-[(3-chloro-6,11-dihydro-6-methyldibenzo[c,f][1,2]thiazepin-11-yl)amino]heptanoic acid S,S-dioxide. In a specific embodiment, said polymorph is 7-[(3-chloro-6,11-dihydro-6-methyldibenzo[c,f][1,2]thiazepin-11-yl)amino]heptanoic acid S,S-dioxide Form I. In another specific embodiment, said polymorph is 7-[(3-chloro-6,11-dihydro-6-methyldibenzo[c,f][1,2]thiazepin-11-yl)amino]heptanoic acid S,S-dioxide Form II. In another embodiment, said mammal described above is a human.

In another embodiment, the present invention includes the preparation of a medicament comprising a polymorph of 7-[(3-chloro-6,11-dihydro-6-methyldibenzo[c,f][1,2]thiazepin-11-yl)amino]heptanoic acid S,S-dioxide. Such a medicament can be used for treating depression, irritable bowel syndrome, attention deficit hyperactivity disorder, or asthma, in a mammal in need of such treatment. In another embodiment, said mammal is a human.

Pharmaceutical dosage forms of 7-[(3-chloro-6,11-dihydro-6-methyldibenzo[c,f][1,2]thiazepin-11-yl)amino]heptanoic acid S,S-dioxide polymorphs can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Liquid dosage forms may also be provided by the present invention, including such non-limiting examples as a suspension, solution, syrup, or emulsion.

7-[(3-chloro-6,11-dihydro-6-methyldibenzo[c,f][1,2]thiazepin-11-yl)amino]heptanoic acid S,S-dioxide polymorphs can be administered by controlled or delayed release means. Controlled release pharmaceutical products generally have a common goal of improving drug therapy over that achieved by their non-controlled release counterparts. Ideally, the use of an optimally designed controlled release preparation in medical treatment is characterized by a minimum of API (active pharmaceutical ingredient) substance being employed to cure or control the condition in a minimum amount of time. Advantages of controlled release pharmaceutical compositions generally include: 1) extended activity of the API; 2) reduced dosage frequency; 3) increased patient compliance; 4) usage of less total API; 5) reduction in local or systemic side effects; 6) minimization of API accumulation; 7) reduction in blood level fluctuations; 8) improvement in efficacy of treatment; 9) reduction of potentiation or loss of API activity; and 10) improvement in speed of control of diseases or conditions. (Kim, Cherng-ju, Controlled Release Dosage Form Design, 2 Technomic Publishing, Lancaster, Pa.: 2000).

Typical daily dosage forms of the invention comprise one or more polymorphs of 7-[(3-chloro-6,11-dihydro-6-methyldibenzo[c,f][1,2]thiazepin-11-yl)amino]heptanoic acid S,S-dioxide, in an amount of from about 10.0 mg to about 50.0 mg, from about 12.5 mg to 37.5 mg, or from about 25.0 mg to about 37.5 mg. In a particular embodiment, the 7-[(3-chloro-6,11-dihydro-6-methyldibenzo[c,f][1,2]thiazepin-1-yl)amino]heptanoic acid S,S-dioxide polymorph for use in such a composition is Form I or Form II. The dosage amounts described herein are expressed in amounts of 7-[(3-chloro-6,11-dihydro-6-methyldibenzo[c,f][1,2]thiazepin-11-yl)amino]heptanoic acid S,S-dioxide in its free form and do not include the weight of any water or solvent molecules.

In another embodiment of the invention, a pharmaceutical composition comprising one or more polymorphs of 7-[(3-chloro-6,1,1-dihydro-6-methyldibenzo[c,f][1,2]thiazepin-11-yl)amino]heptanoic acid S,S-dioxide is administered orally as needed in an amount of from about 10.0 mg to about 50.0 mg, from about 12.5 mg to about 50.0 mg, from about 25.0 mg to about 50.0 mg, or from about 37.5 mg to about 50.0 mg 7-[(3-chloro-6,11-dihydro-6-methyldibenzo[c,f][1,2]thiazepin-11-yl)amino]heptanoic acid S,S-dioxide. For example, about 12.5 mg, about 25.0 mg, or about 37.5 mg. In specific embodiments, pharmaceutical compositions comprising one or more polymorphs of 7-[(3-chloro-6,11-dihydro-6-methyldibenzo[c,f][1,2]thiazepin-11-yl)amino]heptanoic acid S,S-dioxide can be administered orally in amounts of about 25.0 mg or about 37.5 mg. The dosage amounts can be administered in single or divided doses. In another embodiment, a daily dose of a pharmaceutical composition comprising one or more polymorphs of 7-[(3-chloro-6,11-dihydro-6-methyldibenzo[c,f][1,2]thiazepin-11-yl)amino]heptanoic acid S,S-dioxide comprises up to about 50.0 mg 7-[(3-chloro-6,11-dihydro-6-methyldibenzo[c,f][1,2]thiazepin-11-yl)amino]heptanoic acid S,S-dioxide. In other embodiments, the present invention is directed to compositions comprising one or more polymorphs of 7-[(3-chloro-6,11-dihydro-6-methyldibenzo[c,f][1,2]thiazepin-11-yl)amino]heptanoic acid S,S-dioxide as described herein and one or more diluents, carriers, and/or excipients suitable for the administration to a mammal for the treatment or prevention of one or more of the conditions described herein. In one embodiment, a controlled release pharmaceutical composition of one or more polymorphs of 7-[(3-chloro-6,11-dihydro-6-methyldibenzo[c,f][1,2]thiazepin-11-yl)amino]heptanoic acid S,S-dioxide requires a less complex mixture of excipients than other pharmaceutical compositions comprising another form of 7-[(3-chloro-6,11-dihydro-6-methyldibenzo[c,f][1,2]thiazepin-11-yl)amino]heptanoic acid S,S-dioxide.

The 7-[(3-chloro-6,11-dihydro-6-methyldibenzo[c,f][1,2]thiazepin-11-yl)amino]heptanoic acid S,S-dioxide polymorphs of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

The 7-[(3-chloro-6,11-dihydro-6-methyldibenzo[c,f][1,2]thiazepin-11-yl)amino]heptanoic acid S,S-dioxide polymorphic forms of the present invention can be characterized, e.g., by the TGA, DSC, IR spectroscopic data, or by any one, any two, any three, any four, any five, any six, any seven, any eight, any nine, any ten, or any single integer number of PXRD 2-theta angle peaks, or by any combination of the data acquired from the analytical techniques described herein.

Although the invention has been described with respect to various embodiments, it should be realized this invention is also capable of a wide variety of further and other embodiments within the spirit and scope of the appended claims.

EXAMPLES

Example 1

7-[(3-chloro-6,11-dihydro-6-methyldibenzo[c,f][1,2]thiazepin-11-yl)amino]heptanoic acid S,S-dioxide Form I Commercially available 7-[(3-chloro-6,11-dihydro-6-methyldibenzo[c,f][1,2]thiazepin-11-yl)amino]heptanoic acid S,S-dioxide sodium salt (103 mg) was dissolved in water. One equivalent HCl was added and the pH was adjusted to 5.5 with additional HCl (measured by pH paper). The solution turned cloudy. Methanol was added until the solution became clear. The solution was warmed while blowing nitrogen gas until it clouded. The solution was then heated until it became clear. This was followed by cooling the solution during sonication. Crystallization resulted and the 7-[(3-chloro-6,11-dihydro-6-methyldibenzo[c,f][1,2]thiazepin-11-yl)amino]heptanoic acid S,S-dioxide Form I crystals were collected via centrifuge filtration.

Crystals representative of those obtained by completing the method above were characterized using PXRD, DSC, TGA, and IR spectroscopy. The 7-[(3-chloro-6,11-dihydro-6-methyldibenzo[c,f][1,2]thiazepin-11-yl)amino]heptanoic acid S,S-dioxide Form I crystals exhibit a PXRD diffractogram comprising peaks, for example, at about 5.89, 7.82, 8.93, 10.47, 11.22, 12.66, 13.32, 14.72, 16.26, 16.75, 17.64, 18.03, 18.75, 19.50, 20.48, 21.24, 21.56, 22.58, 23.04, 25.19, 26.54, and about 29.12 degrees 2-theta (See FIG. 1). DSC showed an endothermic transition at about 139 degrees C. (See FIG. 2). TGA showed no substantial weight loss up to about 170 degrees C. (See FIG. 3). An IR spectrum of 7-[(3-chloro-6,11-dihydro-6-methyldibenzo[c,f][1,2]thiazepin-11-yl)amino]heptanoic acid S,S-dioxide Form I was taken using a KBr pressed pellet (See FIG. 4).

Differential Scanning Calorimetry

DSC analysis of each sample was performed using a Q1000 Differential Scanning Calorimeter (TA Instruments, New Castle, Del., U.S.A.), which uses Advantage for QW-Series, version 1.0.0.78, Thermal Advantage Release 2.0 (®2001 TA Instruments-Water LLC), with the following components: QDdv.exe version 1.0.0.78 build 78.2; RHBASE.DLL version 1.0.0.78 build 78.2; RHCOMM.DLL version 1.0.0.78 build 78.0; RHDLL.DLL version 1.0.0.78 build 78.1; an TGA.DLL version 1.0.0.78 build 78.1. In addition, the analysis software used was Universal Analysis 2000 for Windows 95/95/2000/NT, version 3.1E; Build 3.1.0.40 (©2001 TA Instruments-Water LLC), or another version as specified in the drawings or otherwise herein.

For all of the DSC analyses, an aliquot of a sample was weighed into either a standard aluminum pan (Pan part # 900786.091; lid part # 900779.901) or a hermetic aluminum pan (Pan part # 900793.901; lid part # 900794.901 (TA Instruments, New Castle Del. USA)). Non-solvated samples were loaded into standard pans and were sealed either by crimping for dry samples or press fitting for wet samples (such as slurries). Solvated samples (including hydrates) were loaded into hermetic pans and hermetically sealed. The sample pan was loaded into the Q 1000 Differential Scanning Calorimeter, which is equipped with an autosampler, and a thermogram was obtained by individually heating the same using the control software at a rate of 11° C./minute from $T_{min}$ (typically 30° C.) to $T_{max}$ (typically 300° C.) using an empty aluminum pan as a reference. Dry nitrogen (compressed nitrogen, grade 4.8 (BOC Gases, Murray Hill, N.J. USA)) was used as a sample purge gas and was set at a flow rate of 50 mL/minute. Thermal transitions were viewed and analyzed using the analysis software provided with the instrument.

Thermogravimetric Analysis

Thermogravimetric analysis (TGA) of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E; Build 3.1.0.40 (2001 TA Instruments-Water LLC), or another version as specified in the drawings or otherwise herein.

For the TGA experiments, the purge gas used was dry nitrogen, the balance purge was 40 mL/minute $N_2$, and the sample purge was 60 mL/minute $N_2$.

TGA was performed on the sample by placing a sample of the 7-[(3-chloro-6,11-dihydro-6-methyldibenzo[c,f][1,2]thiazepin-11-yl)amino]heptanoic acid S,S-dioxide polymorph in a platinum pan. The starting temperature was typically 20 degrees C. with a heating rate of 10 degrees C./minute, and the ending temperature was 300 degrees C.

IR Spectroscopy

IR spectra were obtained using Nexus™ 470 FT-IR, Thermo-Nicolet, 5225 Verona Road, Madison, Wis. 53711-4495 and were analyzed with Control and Analysis software: OMNIC, Version 6.0a, (C) Thermo-Nicolet, 1995-2004. Unless otherwise noted, all IR spectra are obtained at about room temperature (about 24 degrees C. to about 25 degrees C.).

Powder X-Ray Diffraction

Powder x-ray diffraction patters were obtained using a D/Max Rapid X-ray Diffractometer (Rigaku/MSC, The Woodlands, Tex., U.S.A.).

The D/Max Rapid X-ray Diffractometer was equipped with a copper source ($Cu/K_\alpha$ 1.5406 Å), manual x-y stage, and 0.3 mm collimator. A sample was loaded into a 0.3 mm quartz capillary tube (Charles Supper Company, Natick, Mass., U.S.A.) by sectioning off the closed end of the tube and tapping the small, open end of the capillary tube into a bed of the powdered sample or into the sediment of a slurried sample. The loaded capillary tube was mounted in a holder that was placed and fitted into the x-y stage. A diffractogram was acquired using control software (RINT Rapid Control Software, Rigaku Rapid/XRD, version 1.0.0 (©1999 Rigaku Co.)) under ambient conditions at a power setting of 46 kV at 40 mA in transmission mode, while oscillating about the omega-axis from 0-5 degrees at 1 degree/second, and spinning about the phi-axis over 360 degrees at 2 degrees/second. The exposure time was 15 minutes unless otherwise specified.

The diffractogram obtained was integrated of 2-theta from 2-40 degrees and chi (1 segment) from 0-36 degrees at a step size of 0.02 degrees using the cyllnt utility in the RINT Rapid display software (RINT Rapid display software, version 1.18 (Rigaku/MSC)) provided by Rigaku with the instrument. The dark counts value was set to 8 as per the system calibration by Rigaku. No normalization or omega, chi, or phi offsets were used for the integration. The diffractograms included herein show raw data (no background subtraction).

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, or by about +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta. Unless otherwise noted, all diffractograms are obtained at about room temperature (about 24 degrees C. to about 25 degrees C.).

Example 2

7-[(3-chloro-6,11-dihydro-6-methyldibenzo[c,f][1,2]
thiazepin-11-yl)amino]heptanoic acid S,S-dioxide
Form II The resultant crystals produced from the procedure described in Example 1 were placed in methanol and heated until dissolved. Upon dissolution, a clear solution with a faint yellowish-brown color resulted. The solution was allowed to cool to room temperature. Crystals began to form. The volume was reduced via evaporation with nitrogen gas. 7-[(3-chloro-6,11-dihydro-6-methyldibenzo[c,f][1,2]thiazepin-11-yl)amino]heptanoic acid S,S-dioxide Form II crystals were collected via centrifuge filtration.

Crystals representative of those obtained by completing the method above were characterized using PXRD, DSC, TGA, and IR spectroscopy. The 7-[(3-chloro-6,11-dihydro-6-methyldibenzo[c,f][1,2]thiazepin-11-yl)amino]heptanoic acid S,S-dioxide Form II crystals exhibit a PXRD diffractogram comprising peaks, for example, at about 8.52, 10.46, 15.05, 16.40, 16.74, 17.14, 18.22, 20.99, 21.66, 22.68, 23.35, 23.88, 24.55, and about 26.71 degrees 2-theta (See FIG. 5). DSC showed an endothermic transition at about 148 degrees C. (See FIG. 6). TGA showed no substantial weight loss up to about 150 degrees C. (See FIG. 7). An IR spectrum of 7-[(3-chloro-6,11-dihydro-6-methyldibenzo[c,f][1,2]thiazepin-11-yl)amino]heptanoic acid S,S-dioxide Form II was taken using a KBr pressed pellet (See FIG. 8).

What is claimed is:

1. 7-[(3-chloro-6,11-dihydro-6-methyldibenzo[c,f][1,2]thiazepin-11-yl)amino]heptanoic acid S,S-dioxide Form I, wherein said Form I exhibits a powder X-ray diffractogram comprising a peak at about 5.89 degrees 2-theta.

2. 7-[(3-chloro-6,11-dihydro-6-methyldibenzo[c,f][1,2]thiazepin-11-yl)amino]heptanoic acid S,S-dioxide Form I, wherein said Form I exhibits a powder X-ray diffractogram comprising a peak at about 7.82 degrees 2-theta.

3. 7-[(3-chloro-6,11-dihydro-6-methyldibenzo[c,f][1,2]thiazepin-11-yl)amino]heptanoic acid S,S-dioxide Form I of claim 2, wherein said Form I exhibits a powder X-ray diffractogram further comprising peaks at about 8.93 degrees 2-theta.

4. 7-[(3-chloro-6,11-dihydro-6-methyldibenzo[c,f][1,2]thiazepin-11-yl)amino]heptanoic acid S,S-dioxide Form I of claim 1, wherein said Form I exhibits a powder X-ray diffractogram further comprising peaks at about 7.82, and about 8.93 degrees 2-theta.

5. 7-[(3-chloro-6,11-dihydro-6-methyldibenzo[c,f][1,2]thiazepin-11-yl)amino]heptanoic acid S,S-dioxide Form I, wherein said Form I exhibits a powder X-ray diffractogram comprising peaks at about 12.66, about 13.32, about 16.26, and about 17.64 degrees 2-theta.

6. 7-[(3-chloro-6,11-dihydro-6-methyldibenzo[c,f][1,2]thiazepin-11-yl)amino]heptanoic acid S,S-dioxide Form I of claim 4, wherein said Form I exhibits a powder X-ray diffractogram further comprising peaks at about 12.66, about 13.32, and about 17.64 degrees 2-theta.

7. 7-[(3-chloro-6,11-dihydro-6-methyldibenzo[c,f][1,2]thiazepin-11-yl)amino]heptanoic acid S,S-dioxide Form I, wherein said Form I exhibits a powder X-ray diffractogram comprising peaks at about 5.89, about 7.82, about 8.93, about 12.66, about 13.32, about 14.72, about 16.26, about 17.64, about 19.50, about 21.56, about 22.58, and about 25.19 degrees 2-theta.

8. 7-[(3-chloro-6,11-dihydro-6-methyldibenzo[c,f][1,2]thiazepin-11-yl)amino]heptanoic acid S,S-dioxide Form I, wherein said Form I exhibits a DSC thermogram comprising an endothermic transition at about 139 degrees C.

9. 7-[(3-chloro-6,11-dihydro-6-methyldibenzo[c,f][1,2]thiazepin-11-yl)amino]heptanoic acid S,S-dioxide Form II, wherein said Form II exhibits a powder X-ray diffractogram comprising a peak at about 8.52 degrees 2-theta.

10. 7-[(3-chloro-6,11-dihydro-6-methyldibenzo[c,f][1,2]thiazepin-11-yl)amino]heptanoic acid S,S-dioxide Form II, wherein said Form II exhibits a powder X-ray diffractogram comprising a peak at about 10.46 degrees 2-theta.

11. 7-[(3-chloro-6,11-dihydro-6-methyldibenzo[c,f][1,2]thiazepin-11-yl)amino]heptanoic acid S,S-dioxide Form II of claim 9, wherein said Form II exhibits a powder X-ray diffractogram further comprising peaks at about 10.46 degrees 2-theta.

12. 7-[(3-chloro-6,11-dihydro-6-methyldibenzo[c,f][1,2]thiazepin-11-yl)amino]heptanoic acid S,S-dioxide Form II, wherein said Form II exhibits a powder X-ray diffractogram comprising peaks at about 15.05, about 17.14, and about 20.99 degrees 2-theta.

13. 7-[(3-chloro-6,11-dihydro-6-methyldibenzo[c,f][1,2]thiazepin-11-yl)amino]heptanoic acid S,S-dioxide Form II of claim 11, wherein said Form II exhibits a powder X-ray diffractogram further comprising peaks at about 15.05, and about 17.14 degrees 2-theta.

14. 7-[(3-chloro-6,11-dihydro-6-methyldibenzo[c,f][1,2]thiazepin-11-yl)amino]heptanoic acid S,S-dioxide Form II of claim 13, wherein said Form II exhibits a powder X-ray diffractogram further comprising peaks at about 20.99, and about 21.66 degrees 2-theta.

15. 7-[(3-chloro-6,11-dihydro-6-methyldibenzo[c,f][1,2]thiazepin-11-yl)amino]heptanoic acid S,S-dioxide Form II, wherein said Form II exhibits a powder X-ray diffractogram comprising peaks at about 8.52, about 10.46, about 15.05, about 17.14, about 18.22, about 20.99, about 21.66, about 22.68, about 23.35, about 23.88, about 24.55, and about 26.71 degrees 2-theta.

16. 7-[(3-chloro-6,11-dihydro-6-methyldibenzo[c,f][1,2]thiazepin-11-yl)amino]heptanoic acid S,S-dioxide Form II, wherein said Form II exhibits a DSC thermogram comprising an endothermic transition at about 148 degrees C.

17. A method of making a polymorph of 7-[(3-chloro-6,11-dihydro-6-methyldibenzo[c,f][1,2]thiazepin-11-yl)amino]heptanoic acid S,S-dioxide of claim 7, comprising:
    (a) providing 7-[(3-chloro-6,11-dihydro-6-methyldibenzo[c,f][1,2]thiazepin-11-yl)amino]heptanoic acid S,S-dioxide sodium salt; and
    (b) contacting said 7-[(3-chloro-6,11-dihydro-6-methyldibenzo[c,f][1,2]thiazepin-11-yl)amino]heptanoic acid S,S-dioxide sodium salt with an appropriate acid so as to desalify said sodium salt;
    (c) contacting the desalified mixture from step (b) with an appropriate solvent; and (d) crystallizing said polymorph of 7-[(3-chloro-6,11-dihydro-6-methyldibenzo[c,f][1,2]thiazepin-11-yl)amino]heptanoic acid S,S-dioxide.

18. A method of making a polymorph of 7-[(3-chloro-6,11-dihydro-6-methyldibenzo[c,f][1,2]thiazepin-11-yl)amino]heptanoic acid S,S-dioxide of claim 15, comprising:
(a) providing 7-[(3-chloro-6,11-dihydro-6-methyldibenzo[c,f][1,2]thiazepin-11-yl)amino]heptanoic acid S,S-dioxide Form I;
(b) contacting said 7-[(3-chloro-6,11-dihydro-6-methyldibenzo[c,f][1,2]thiazepin-11-yl)amino]heptanoic acid S,S-dioxide Form I with an appropriate solvent; and
(c) crystallizing said polymorph of 7-[(3-chloro-6,11-dihydro-6-methyldibenzo[c,f][1,2]thiazepin-11-yl)amino]heptanoic acid S,S-dioxide.

19. A method of treating a mammal suffering from depression, irritable bowel syndrome, attention deficit hyperactivity disorder, or asthma, comprising administering to said mammal an effective amount of the 7-[(3-chloro-6,11-dihydro-6-methyldibenzo[c,f][1,2]thiazepin-11-yl)amino]heptanoic acid S,S-dioxide Form I of claim 4.

20. A method of treating a mammal suffering from depression, irritable bowel syndrome, attention deficit hyperactivity disorder, or asthma, comprising administering to said mammal an effective amount of the 7-[(3-chloro-6,11-dihydro-6-methyldibenzo[c,f][1,2]thiazepin-11-yl)amino]heptanoic acid S,S-dioxide Form II of claim 15.

* * * * *

UNITED STATES PATENT AND TRADEMARK OFFICE
CERTIFICATE OF CORRECTION

| | | |
|---|---|---|
| PATENT NO. | : 8,367,656 B2 | Page 1 of 1 |
| APPLICATION NO. | : 12/041747 | |
| DATED | : February 5, 2013 | |
| INVENTOR(S) | : Sansone | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 936 days.

Signed and Sealed this
Twenty-fifth Day of November, 2014

Michelle K. Lee
*Deputy Director of the United States Patent and Trademark Office*